US008987215B2

(12) United States Patent
Taylor et al.

(10) Patent No.: US 8,987,215 B2
(45) Date of Patent: Mar. 24, 2015

(54) COMPOSITION FOR USE IN GENE THERAPY

(75) Inventors: Catherine Taylor, Trondheim (NO); Kurt Ingar Draget, Trondheim (NO)

(73) Assignee: NTNU Technology Transfer AS, Trondheim (NO)

( * ) Notice: Subject to any disclaimer, the term of this patent is extended or adjusted under 35 U.S.C. 154(b) by 719 days.

(21) Appl. No.: 13/259,124

(22) PCT Filed: Mar. 23, 2010

(86) PCT No.: PCT/GB2010/000534
§ 371 (c)(1),
(2), (4) Date: Dec. 7, 2011

(87) PCT Pub. No.: WO2010/109176
PCT Pub. Date: Sep. 30, 2010

(65) Prior Publication Data
US 2012/0076853 A1 Mar. 29, 2012

(30) Foreign Application Priority Data

Mar. 23, 2009 (GB) .................................. 0904941.2

(51) Int. Cl.
A01N 43/04 (2006.01)
A61K 31/70 (2006.01)
C12N 15/11 (2006.01)
A61K 31/715 (2006.01)
A61K 31/337 (2006.01)
A61K 9/00 (2006.01)
A61K 9/127 (2006.01)
A61K 31/7048 (2006.01)
C12N 15/88 (2006.01)
A61K 47/26 (2006.01)
A61K 48/00 (2006.01)

(52) U.S. Cl.
CPC ............. A61K 31/337 (2013.01); A61K 9/0019 (2013.01); A61K 9/1272 (2013.01); A61K 31/7048 (2013.01); C12N 15/88 (2013.01); A61K 47/26 (2013.01); A61K 48/00 (2013.01)
USPC ................................ 514/23; 514/44 A; 514/54

(58) Field of Classification Search
CPC . C12N 15/88; A61K 31/7048; A61K 31/337; A61K 47/26; A61K 48/00; A61K 9/1272; A61K 9/0019
See application file for complete search history.

(56) References Cited

U.S. PATENT DOCUMENTS

| 4,225,592 | A | 9/1980 | Lakatos et al. |
| 5,166,137 | A | 11/1992 | Otterlei et al. |
| 5,459,054 | A | 10/1995 | Skjak-Braek et al. |
| 5,460,957 | A | 10/1995 | Hiura et al. |
| 5,683,991 | A | 11/1997 | Guggenbichler et al. |
| 5,759,572 | A | 6/1998 | Sugimoto et al. |
| 5,795,587 | A | 8/1998 | Gao et al. |
| 6,121,441 | A | 9/2000 | Simensen et al. |
| 6,339,075 | B1 | 1/2002 | King et al. |
| 6,407,226 | B1 * | 6/2002 | Simensen et al. ............. 536/124 |
| 6,440,314 | B1 | 8/2002 | Simpson |
| 6,440,413 | B1 | 8/2002 | Hooreman |
| 6,747,015 | B2 | 6/2004 | Byon et al. |
| 8,529,890 | B2 * | 9/2013 | Draget et al. .............. 424/94.61 |
| 2003/0013678 | A1 | 1/2003 | Lang et al. |
| 2003/0022863 | A1 | 1/2003 | Stahl et al. |
| 2003/0059474 | A1 | 3/2003 | Scott et al. |
| 2003/0224070 | A1 | 12/2003 | Sweazy et al. |
| 2004/0073964 | A1 | 4/2004 | Ellington et al. |
| 2004/0224922 | A1 | 11/2004 | King |
| 2005/0158392 | A1 | 7/2005 | Kim et al. |
| 2006/0083780 | A1 | 4/2006 | Heyes et al. |
| 2009/0010914 | A1 | 1/2009 | Taylor et al. |

FOREIGN PATENT DOCUMENTS

| CA | 2 428 473 A1 | 5/2002 |
| DE | 268865 A1 | 6/1989 |
| DE | 19520743 A1 | 12/1996 |
| EP | 324720 A1 | 7/1989 |
| EP | 506325 A1 | 9/1992 |
| EP | 0888778 A1 | 1/1999 |
| EP | 1234584 | 8/2002 |
| EP | 1714660 A1 | 10/2006 |
| EP | 1745705 A1 | 1/2007 |
| EP | 1837018 A1 | 9/2007 |
| FR | 7576 M | 1/1970 |
| GB | 1042379 | 9/1966 |
| GB | 2 430 881 A1 | 4/2007 |
| JP | 61-076413 | 4/1986 |
| JP | 01-197431 | 8/1989 |
| JP | 09208472 A | 8/1997 |

(Continued)

OTHER PUBLICATIONS

U.S. Appl. No. 60/150,160, filed Aug. 1999, Wolff et al.*
Hanninen, A. and Harrison, L.C. 2004 "Mucosal Tolerance to Prevent Type 1 Diabetes: Can the Outcome Be Improved in Humans?" *Rev Diabet Stud* 1: 113-121.
Merck Manual, "Disorders," www.merckmanuals.com/professional/index.html, accessed Aug. 6, 2012.
Merck Manual, "Diseases," www.merckmanuals.com/professional/index.html, accessed Aug. 6, 2012.
Merck Manual, "Diabetes," www.merckmanuals.com/professional/index.html, accessed Aug. 6, 2012.
Chono, S. et al. 2008 "An efficient and low immunostimulatory nanoparticle formulation for systemic siRNA delivery to the tumor" *Journal of Controlled Release* 131: 64-69.

(Continued)

Primary Examiner — Lawrence E Crane
(74) Attorney, Agent, or Firm — Knobbe, Martens, Olson & Bear, LLP

(57) ABSTRACT

A composition useful in gene therapy and a method of treatment to effect gene therapy is provided. In particular, a pharmaceutical composition comprising a nonimmunogenic net polyanionic oligosaccharide, such as an oligouronate, associated with a particulate complex of an anionic nucleic acid material and a cationic macromolecule, optionally together with at least one pharmaceutical carrier or excipient, is provided.

13 Claims, 2 Drawing Sheets

(56) References Cited

FOREIGN PATENT DOCUMENTS

| | | |
|---|---|---|
| JP | 2000-034302 | 2/2000 |
| JP | 2002-338493 A | 11/2002 |
| JP | 2005-145885 | 6/2005 |
| JP | 2006-028041 | 2/2006 |
| WO | WO 88/09794 A1 | 12/1988 |
| WO | WO 91/07951 A1 | 6/1991 |
| WO | WO 91/11205 A1 | 8/1991 |
| WO | WO 95/18145 A1 | 7/1995 |
| WO | WO 98/13024 A2 | 4/1998 |
| WO | WO 01/15672 A2 | 3/2001 |
| WO | WO 01/17506 A1 | 3/2001 |
| WO | WO 01/66084 A2 | 9/2001 |
| WO | WO 01/72278 A2 | 10/2001 |
| WO | WO 2007/02224 A2 | 1/2004 |
| WO | WO 2005/089722 A1 | 9/2005 |
| WO | WO 2007/039754 A1 | 4/2007 |
| WO | WO 2007/039760 A2 | 4/2007 |
| WO | WO 2007/046719 A2 | 4/2007 |
| WO | WO 2008/125828 A2 | 10/2008 |
| WO | WO 2008/137114 A1 | 11/2008 |
| WO | WO 2009/142892 A2 | 11/2009 |

OTHER PUBLICATIONS

Dalby, B. et al. 2004 "Advanced transfection with Lipofectamine 2000 reagent: primary neurons, siRNA, and high-throughput applications" *Methods* 33: 95-103.

Jiang, G. et al. 2007 "DNA/PEI/Alginate polyplex as an efficient in vivo gene delivery system" *Biotechnology and Bioprocessing Engineering* 12: 684-689.

Klöck, G. et al. 1997 "Biocompatibility of mannuronic acid-rich alginates" *Biomaterials* 18: 707-713.

Kong, H. J. et al. 2008 "Design of Biodegradable Hydrogel for the Local and Sustained Delivery of Angiogenic Plasmid DNA" *Pharaceutical Research* 25: 1230-1238.

Krebs, M. D. et al. 2009 "Localized and Sustained Delivery of Silencing RNA from Macroscope Biopolymer Hydrogels" *Journal of the American Chemical Society* 131: 9204-9206.

Rakkhithawatthana, V. et al. 2010 "Investigation of gene transferring efficacy through nano-polyplex consisting of methylated N-(4-pyridinylmethyl) chitosan chloride and poly(ethylenimine) in human cell lines" *Carbohydrate Polymers* 80: 276-284.

Sioud, M. et al. 2003 "Cationic liposome-mediated delivery of siRNAS in adult mice" *Biochemical and Biophysical Research Communications* 312: 1220-1225.

Yun, Y. H. et al. 2004 "Hyaluronan microspheres for sustained gene delivery and site-specific targeting" *Biomaterials* 25: 147-157.

Westedt, U. et al. 2007 "Poly(vinylalcohol)-graft-poly(lactide-co-glycolide) nanoparticles for local delivery of paclitaxel for restenosis treatment" *Journal of Controlled Release* 119: 41-51.

Aikiyama, Hisayoshi et al. (1991) "Effect of Depolymerized Alginates on the Growth of Bifidobacteria" *Biosci. Biotech. Biochem* 56: 355-356.

Banning D. et al. 1997 "Oscillatory and thermorheological characterization of alginate/mucin mixes" Pharmacy and Pharmacology (British Pharmaceutical Conference 1997 Science proceedings 134th meeting, Scarborough, Sep. 15-18, 1997, Abstract 65.

Eiselt, Petra et al. (2000) "Porous carriers for biomedical applications based on alginate hydrogels" *Biomaterials* 21: 1921-1927.

Fiel, Stanley B. et al. (1995) "Comparison of Three Jet Nebulizer Aerosol Delivery Systems Used to Administer Recombinant Human DNase I to Patients With Cystic Fibrosis" *CHEST Official Publication of the American College of chest Physicians* 108: 153-156.

Murata, K. et al. 1992 "Continuous depolymerization of alginates by a non-support bioreactor system containing flocculated bacterial cells" *Journal of Fermentation and Bioengineering* 73:172-174.

Pandey, Rajesh & Khuller, G.K. (2005) "Chapter 27: Alginate as a Drug Delivery Carrier" *Handbook of Carbohydrate Engineering* pp. 799-815.

Tadashi, Yoshimatsu et al. (2002) "Effects on Intestinal Flora of a Beverage Containing Non-fermentable Depolymerized Sodium Alginate and Water-soluable Fermentable Corn Bran Fiber" *The Journal of Nutrition and Dietetics* 60: 137-143.

Tang, J.X. et al. 2005 "Anionic poly(amino acid)s dissolve F-actin and DNA bundles, enhance DNase activity, and reduce the viscosity of cystic fibrosis sputum" *Am J Physiol Lung Cell Mol Physiol* 289: L599-L605.

Terada, A. et al. (1995) "Effect of Dietary Alginate on the Faecal Microbiota and Faecal Metabolic Activity in Humans" *Microbial Ecology in Health and Disease* 8: 259-266.

Grasdalen, H. et al. 1979 "A.P.M.R. study of the composition and sequence of urinate residues in alginates" *Carbohydrate Research* 68: 23-31.

FMC Biopolymer 2003 "A world of possibilities lies just below the surface: Alginates" Brochure (in 20 pages).

Ikeda, A. and Ono T.H. 2000 "Preparation of low-molecular weight alginic acid by acid hydrolysis" *Carbohydrate Polymers* 42: 421-425.

Shidrawi, R.G.et al. 2002;"Emergency colonoscopy for distal intestinal obstruction syndrome in cystic fibrosis patients", *Gut*; 51: 285-286.

Shraishi, S. et al. J., 1991: "Improvement of Absorption Rate of Indomethacin and Reduction of Stomach Irritation by Alginate Dispersions" *J Pharm. Pharmacol* 43: 615-620.

Iwamoto, M. et al. 2005 "Structure—activity relationship of alginate oligosaccharides in the induction of cytokine production from RAW264.7 cells" *FEBS Letters* 579: 4423-4429.

Witschi, C. et al. 1999 "In vitro evaluation of microparticles and polymer gels for use as nasal platforms for protein delivery" *Pharmaceutical Research* 16: 382-390.

\* cited by examiner

COMPOSITION FOR USE IN GENE THERAPY

CROSS-REFERENCE TO RELATED APPLICATIONS

This application claims the benefit and priority to and is a U.S. National Phase Application of PCT International Application Number PCT/GB2010/000534, filed on Mar. 23, 2010, designating the United States of America and published in the English language, which is an International Application that claims the benefit of priority to United Kingdom Application No. GB0904941.2, filed on Mar. 23, 2009.

FIELD OF THE INVENTION

This invention relates to compositions useful in gene therapy and methods of treatment to effect gene therapy.

BACKGROUND OF THE INVENTION

Gene therapy is a technique which operates by delivering genetic material to endogenous cells within a functioning human or non-human animal body to add additional DNA-driven capacity to those cells, for example to introduce novel genes, to introduce additional copies of pre-existing genes, to impair the functioning of existing genes, or to repair existing but non-functioning genes. To some extent it is comparable to transfection of cells in a cell culture, but since the cells to be treated are part of the complex whole of the animal body, the overall functioning of which must be maintained, gene therapy faces particular problems in terms of the mechanism of delivery of the genetic material to the cells to be treated. To this end, carriers have been used to protect the genetic material from degradation and to facilitate its cellular uptake.

One line of approach has been to take advantage of the life cycle of viruses, which transfer their genetic material into host cells and co-opt the functions of the host cells (or their progeny) to replicate and release copies of the virus. Accordingly viral vectors have been used to transfer desired genetic material into host cells in the animal. Nonetheless, viral vectors have limited capacity to carry bulky DNA and moreover there are concerns over the safety of using viral vectors in gene therapy, especially of humans (see for example Danielsen et al., *Biochimica et Biophysica Acta* 1721: 44-54 (2005)). In 1999, for example, 18-year old Jesse Gelsinger, who was participating in a gene therapy trial for ornithine transcarboxylase deficiency, died from multiple organ failure thought to have been triggered by an immune response to the adenovirus vector that was being used.

Apart from direct injection into the cells to be treated and localised injection coupled with electroporation of the target cells, both of which are of limited utility, there are two primary categories of non-viral delivery systems for genetic material for gene therapy, namely lipoplexes and polyplexes. Lipoplexes are liposomes formed by mixing cationic lipids with anionic DNA and contain the DNA within a protective lipid shell (see for example Torchilin, *Nature Reviews Drug Discovery* 4: 145-160 (2005)). Polyplexes are nanometer-sized self assembled particles comprising a polycationic polymer and the anionic DNA—the polycationic polymer compacts the DNA to form nanoparticles in which the DNA is at least partially protected from enzymes, e.g. extracellular nucleases, which would otherwise degrade it. (See for example De Smet et al., *Pharmaceutical Research* 17: 113-126 (2000)).

Both lipoplexes and polyplexes are formed by electrostatic interactions and have a surface net positive electric charge. This net charge has the advantages of preventing the particles from clumping into aggregates and assisting in promoting cellular uptake, but has the disadvantage that the particles are vulnerable to undesired electrostatic interaction with endogenous anionic extracellular biomolecules (see Remaut et al., *Materials Science and Engineering* 58: 117-161 (2007)).

Indeed, in general, unless the genetic material can be injected directly into the target cells, which, as mentioned, is of limited feasibility in gene therapy, the genetic material faces a host of barriers between administration and cellular uptake. If administered alone, it is liable to destruction before uptake, for example by extracellular nucleases, while if it is administered as a complex that complex must overcome such barriers as blood, interstitium and mucosal layers before genetic material uptake occurs. While viruses naturally have systems for overcoming these barriers, as mentioned above there are serious problems associated with viral vectors. These barriers, or "extracellular matrices", and their components may dramatically alter the surface properties of the DNA complexes, potentially inducing their aggregation or destruction, or causing their immobilization, or altering their ability to undergo cellular uptake upon arrival at the target cells. Such interactions, moreover, may activate the complement system and immune response, further reducing the chances of successful, side-effect free, delivery of the genetic material to the target cells.

As a result, surface coating of the complexes with camouflaging materials, such as PEG, which provoke little or no response has been proposed. This too, however, suffers from drawbacks. Thus, for example, lipoplexes prepared with PEGylated lipids tend to carry the DNA unprotected on their surfaces rather than inside, and so the liposomes must instead be PEGylated post-production. Additionally, PEGylation interferes with DNA release from lipoplexes and may cause generation of anti-PEG antibodies, which will limit therapy to a single round of treatment.

There thus remains a continuing need for an improved manner of delivery of genetic material for gene therapy.

SUMMARY OF THE INVENTION

We have now found that an alternative to PEGylation for camouflage coating of DNA complexes, such as lipoplexes and polyplexes, is provided by the use of net polyanionic oligosaccharides, and in particular by the use of oligouronates or anti-coagulant oligosaccharides, e.g. heparinoids, and other non-immunogenic net polyanionic oligosaccharides.

Thus viewed from one aspect the invention provides a parenteral pharmaceutical gene therapy composition comprising a non-immunogenic net polyanionic oligosaccharide associated with a particulate complex of an anionic nucleic acid material and a cationic macromolecule, optionally together with at least one pharmaceutical carrier or excipient.

Viewed from a further aspect the invention provides the use of a non-immunogenic net polyanionic oligosaccharide for the manufacture of a composition according to the invention for use in parenteral gene therapy of a human or non-human vertebrate (especially mammalian) animal subject.

Figure 1A:
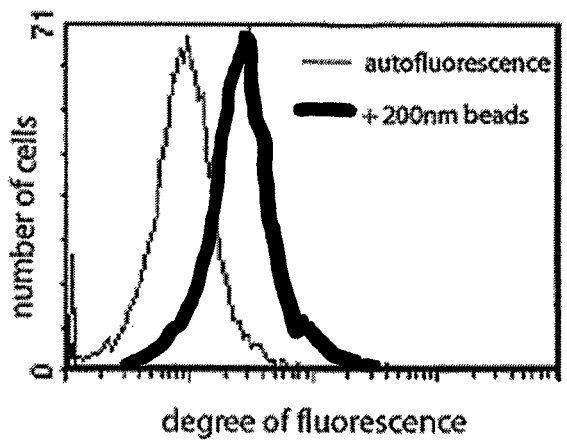
FIGS. 1A-1C show the uptake of microbeads into mucus-secreting cells with or without a continuous mucus layer and the effect of polyanionic oligosaccharide treatment.

Viewed from another aspect the invention provides a method of gene therapy of a human or non-human vertebrate (especially mammalian) animal subject which method comprises parenterally administering to said subject an effective amount of a composition according to the invention.

DETAILED DESCRIPTION OF THE SPECIFIC EMBODIMENTS

In the compositions of the invention, the particulate complex may be any conventional combination of a functional anionic nucleic acid material, e.g. DNA containing an operative gene or operative for correction of an endogenous gene, and a macromolecular cationic protective material, e.g. a liposome-forming lipid or a polycationic material capable of forming a polyplex with the nucleic acid material. Lipoplexes and polyplexes such as have been described in the literature, and their analogs containing different genetic material or lipids or polycations, may be used as starting materials for the preparation of the composition of the invention. Suitable nucleic acid for use according to the invention includes DNA and RNA, e.g. siRNA.

The compositions of the invention may thus be prepared by contacting, in sterile aqueous solution, the genetic material/cationic agent particulate and an excess of the net polyanionic oligosaccharide, and retrieving and, if desired, washing, drying and reformulating the oligosaccharide-associated particulate.

By net polyanionic is meant that the oligosaccharide should have a plurality of anionic groups and that it should carry a net negative charge. In this way, electrostatic interaction causes spontaneous association of the oligosaccharide with, for example, a lipoplex or polyplex.

The charge of the oligosaccharide reduces undesired interactions with charged extracellular biomolecules is reduced or eliminated. Since many oligosaccharides, such as oligouronates and heparinoids, are essentially non-immunogenic and do not cause blood coagulation, other undesired effects of conventional or PEGylated lipoplexes and polyplexes are reduced or avoided. Moreover, especially where the oligosaccharide is an oligouronate, or a mixture comprising an oligouronate, the oligouronate may interact with mucosal barriers both to prevent entrapment of the particles and to facilitate their penetration through the mucosal layers.

By use of an oligosaccharide, rather than a polysaccharide, the stability of the polyplex/lipoplex is not compromised and, in the case of oligouronates, the ability to modify mucosal rheology, is enhanced. Thus, the oligosaccharide used is preferably a 3- to 50-mer, more especially a 3- to 28-mer.

While the oligosaccharide, which preferably is linear, may be a synthetic material, it is preferably a derivative, having a weight average molecular weight of less than 100,000 Da, of a naturally occurring polysaccharide. It is preferably a 3- to 28-mer, e.g. a 20-mer, in particular a 4- to 25-mer, especially a 6- to 22-mer, in particular an 8- to 15-mer, especially a 10-mer, e.g. having a molecular weight in the range 350 to 6,000 Da, especially 750 to 4,500 Da. It may be a single compound or it may be a mixture of oligosaccharides, preferably majoritatively or exclusively oligouronates, e.g. of a range of degrees of polymerization. Moreover, the monomeric residues in the oligosaccharides, i.e. the monosaccharide groups, may be the same or different.

In a preferred embodiment, the oligosaccharide used has no appreciable viscosity above that of the solvent, e.g. the oligosaccharide has a, viscosity of less than 20 cP, preferably less than 15 cP, when measured under standard conditions (C=1%, $H_2O$).

Low and very low molecular weight heparins and heparinoids are readily available commercially.

Oligouronates are readily accessible from natural sources since many natural polysaccharides contain uronic acid residues such as guluronic and galacturonic acid residues.

Polysaccharide to oligosaccharide cleavage to produce oligouronates useable according to the present invention may be performed using conventional polysaccharide lysis techniques such as enzymatic digestion and acid hydrolysis. Oligouronates may then be separated from the polysaccharide breakdown products chromatographically using an ion exchange resin or by fractionated precipitation or solubilization.

Examples of polysaccharides containing uronates include naturally occurring polysaccharides (such as xanthan, pectin, alginates, hyaluronan, heparin and chondroitin sulphate) and chemically modified polysaccharides, including but not limited to polysaccharides modified to add charged groups (such as carboxylated or carboxymethylated glycans), and polysaccharides modified to alter flexibility (e.g. by periodate oxidation). Suitable polysaccharides are discussed for example in "Handbook of Hydrocolloids", Ed. Phillips and Williams, CRC, Boca Raton, Fla., USA, 2000. The use of alginates however is especially preferred as these naturally occur as block copolymers of manuronic (M) and guluronic (G) acids and G-block oligomers can readily be produced from alginate source materials. Indeed, in general the oligouronate is preferably an oligoguluronic acid, or less preferably an oligogalacturonic acid.

Where alginates are used as the starting material for preparation of the oligouronate, the guluronic acid content may if desired be increased by epimerization with mannouronan C-5 epimerases from *A. vinelandii*.

Oligoguluronic acids suitable for use according to the invention may conveniently be produced by acid hydrolysis of alginic acid from *Laminaria hyperborea*, dissolution at neutral pH, addition of mineral acid to reduce the pH to 3.4 to precipitate the oligoguluronic acid, washing with weak acid, resuspension at neutral pH and freeze drying.

The use of oligouronates of the type described in WO2008/125828, the contents of which are hereby incorporated by reference, is especially preferred.

The counterions for the oligouronates may be any of the physiologically tolerable ions commonly used for charged drug substances, e.g. sodium, potassium, ammonium, chloride, mesylate, meglumine, etc. Ions which promote alginate gelation, e.g. group 2 metals, however will preferably not be used. Such group 2 ions will desirably also be essentially absent from the other components of the compositions of the invention.

Experiments have shown that the presence of oligosaccharides, such as G-block oligouronates, does not reduce cellular uptake of the genetic material.

The conditions to be treated using the method of the invention may be any conditions capable of treatment by gene therapy and the choice of the genetic material to be used will clearly depend upon the particular condition.

Examples of conditions which may be treated include cancers (e.g. myeloid disorders), thalassemia, cystic fibrosis, deafness, vision disorders (e.g. Leber's congenital amaurosis), diabetes, Huntingdon's disease, X-linked severe combined immunodeficiency disease, heart disease and ornithine transcarboxylase deficiency. Alternatively the gene therapy may be used to introduce non-endogenous genes, e.g. genes for bioluminescence, or to introduce genes which will knock out endogenous genes, e.g. genes coding for mRNA fragments which will bind to and prevent transcription of endogenous mRNA, for example to produce test animals having particular susceptibilities or simply to reduce expression of an over-expressed gene.

The mode of administration of the compositions of the invention may be any parenteral route, e.g. by pulmonary or nasal administration, injection, infusion or depot placement, typically inhalation, subcutaneous, intramuscular, or by intravenous injection, or direct injection into an organ of concern. The range and dosage regime may be those conventional for the particular gene therapy.

The compositions of the invention will generally be in dry powder form or suspension, e.g. in (sterile) water for nebulisation or injections. The compositions may include further physiologically tolerable carriers or excipients, e.g. carriers, solvents, dispersants, antioxidants, osmolality adjustors, pH modifiers, viscosity modifiers, etc.

Besides liposomes and particulate complexes containing genetic material, the invention is also applicable to liposomes and particulate complexes and other vesicles having a surface positive charge which carry other drug substances, for example paclitaxel and amphotericin B. For paclitaxel, in particular, the use as a carrier for parenteral administration of oligosaccharide-associated cationic surface charged vesicles offers the opportunity to avoid the use of the current, dosage-limiting, Cremophors. Such other compositions and their use form further aspects of the present invention. Viewed from this aspect the invention provides a parenteral pharmaceutical composition comprising vesicles (e.g. liposomes) containing a drug substance and having a cationic shell material, and external to said vesicles a non-immunogenic net polyanionic oligosaccharide, said composition optionally further containing a pharmaceutical carrier or excipient.

Such vesicles may be prepared in conventional fashion using conventional cationic shell-forming agents, e.g. phospholipids such as 1,2-dioleoyl-sn-glycero-3-ethylphosphocholine (EDOPC). In general, the oligosaccharide will be used in a weight ratio relative to the shell-forming agent of 0.1:1 to 10:1, e.g. 0.5:1 to 2:1.

The invention will now be described with reference to the following non-limiting Examples.

Example 1

Infection Suspension

Nucleic acid (e.g. RNA or DNA, optionally in plasmid form) containing operative coding for the desired protein, i.e. capable of causing protein expression on cellular uptake, is complexed in sterile aqueous physiologically buffered solution with a complexing or transfecting agent (e.g. Lipofectamine™, SuperFect or EDOPC) in a weight ratio of 1:5 to form a polyplex or lipoplex in conventional fashion. Before administration, a sodium guluronate of DP10 (prepared as described in WO2008/125828) is added at a weight ratio relative to the complexing/transfecting agent of 1:1.

Example 2

Infection Suspension

Nucleic acid (e.g. RNA or DNA, optionally in plasmid form) containing operative coding for the desired protein, i.e. capable of causing protein expression on cellular uptake, is complexed in sterile aqueous physiologically buffered solution with chitosan in a ratio of 1:10 nucleic acid base units to chitosan amines. Before administration, a sodium guluronate of DP10 (prepared as described in WO2008/125828) is added at a weight ratio relative to the chitosan of 1:5.

Example 3

Microbead Uptake in Cells with Mucus Layer

The ability of mucus-secreting HT29-MTX cells to take up microbeads was assessed. Cells having a discontinuous mucus layer and cells having a continuous mucus layer were investigated as follows.

HT29-MTX cells (*Clin. Otolaryngol. Allied Sci.* (2003) 28(1):p. 39-42) were grown to confluence in 24 well plates. Dulbecco's Modified Eagle Medium, DMEM (GIBCO) was used. For wells designated confluent, mucus layer cells were grown under 3 µm pore size Transwell™ filters (Corning) and all medium changes were accomplished through the filter membrane to protect the underlying mucus layer.

Growth medium was removed and replaced with 750 µl of fresh medium and 250 µl of either a polyanionic oligosaccharide (G-block having a degree of polymerisation DP=20) or saline (control).

40 µl of Microbeads (FluoSpheres® carboxylate-modified microspheres, 0.02 µm, yellow-green fluorescent; Invitrogen) were added to test wells as a 0.02% suspension.

Incubation was performed at 37° C. for 2 hours and stopped by washing cells (×2) in cold PBS (2 ml). Cold trypsin/EDTA used to detach cells (2 ml), medium was added (2 ml) and the cells were spun down. Cells were washed (×2) in cold PBS (2 ml) and suspended in PBS (0.5 ml).

Flow cytometry was performed with fluorophore excitation using the 488 nm line of an argon laser with detectors optimized for the fluorophore.

Figure 1B:
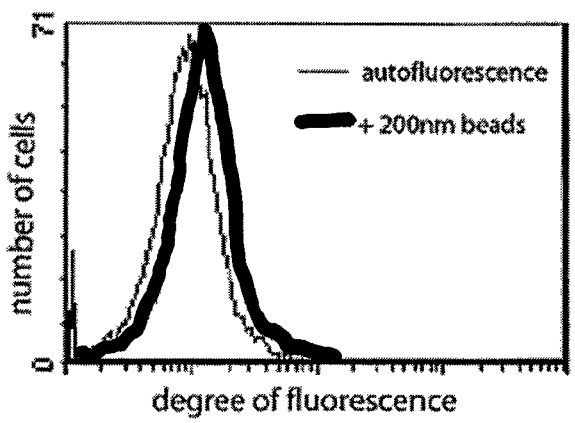
Figure 1C:
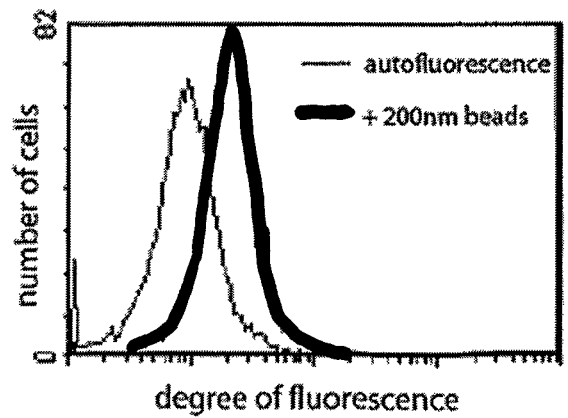

Results of this experiment are shown in FIGS. 1A, 1B and 1C. FIG. 1A shows the uptake of microbeads into cells with a discontinuous mucus layer (without polyanionic oligosaccharide). The left-hand peak is the auto-fluorescence curve and right-hand peak the results of the sample incubated with fluorescent beads. FIG. 1B shows the uptake of microbeads into cells with a continuous mucus layer (without polyanionic oligosaccharide). The left-hand peak is the auto-fluorescence curve and right-hand peak the results of the sample incubated with fluorescent beads. FIG. 1C shows the uptake of microbeads into cells with a continuous mucus layer which were treated with polyanionic oligosaccharide. The left-hand peak is the auto-fluorescence curve and right-hand peak the results of the sample incubated with fluorescent beads and polyanionic oligosaccharide.

These data show that a continuous mucus layer is a barrier to cellular uptake of microbeads. Addition of a polyanionic oligosaccharide significantly increases uptake of microbeads in cells with a continuous mucus layer.

Example 4

Effect of Polyanionic Oligosaccharide on Cellular Uptake of a siRNA Lipoplex

HeLa or HEK cells (commercially available) were grown to confluence in 6 well plates using optiMEM® growth medium (Invitrogen).

The growth medium was removed and replaced with 75 µl of fresh medium and 250 µl of either a polyanionic oligosaccharide (G-block having a degree of polymerisation DP=20) or saline (control).

Fluorescent siRNA/Lipofectamine™ RNAimax lipoplexes (Invitrogen) were then added to test wells according to the manufacturers recommended protocol and incubated at 37° C. for 2 hours. No transfection reagent was added to control wells.

Incubation was stopped by washing cells (×2) in cold PBS (2 ml). Cold trypsin/EDTA was used to detach cells (2 ml), medium was added (2 ml) and the cells were spun down and washed (×2) in cold PBS (2 ml). Cells were then suspended in PBS (0.5 ml).

Flow cytometry was performed with fluorophore excitation using the 488 nm line of an argon laser with detectors optimised for the fluorphore.

Figure 2A:
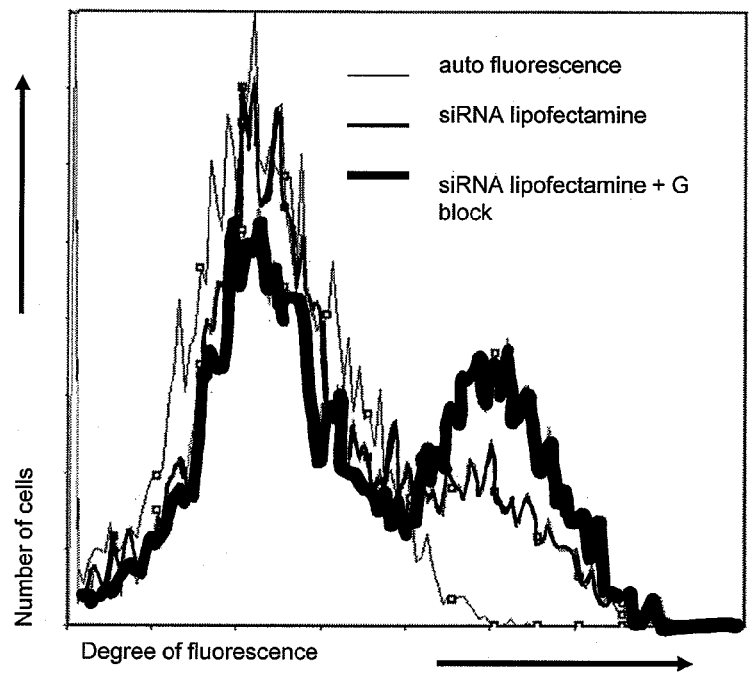
FIGS. 2A-2B show the effect of polyanionic oligosaccharide on the cellular uptake of a siRNA lipoplex in HEK and HeLa cells, respectively.
Figure 2B:
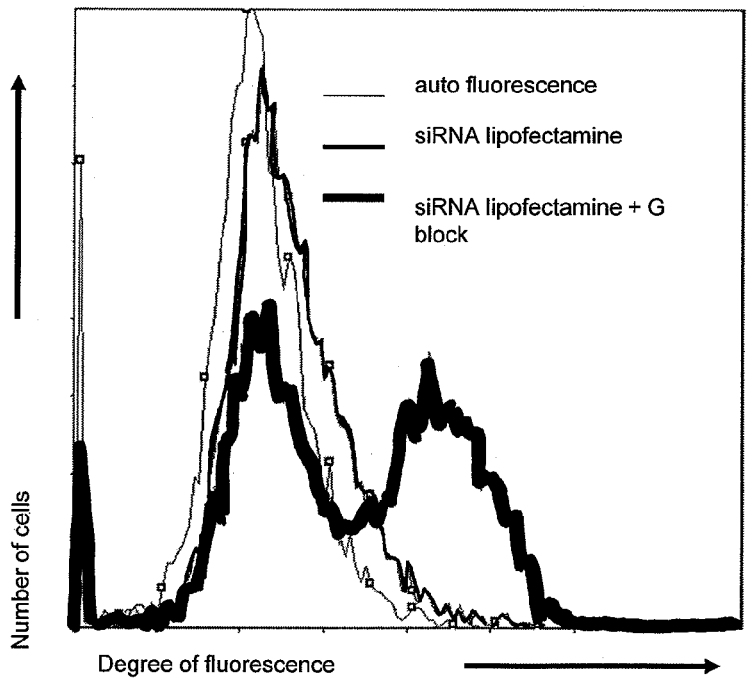

Results of this experiment are shown in FIGS. 2A and 2B. FIG. 2A shows the effect of polyanionic oligosaccharide on transfection of HEK cells—some uptake of nucleic acid is seen in the absence of oligosaccharide (medium thickness line), but greater uptake is observed when oligosaccharide is present (thickest line). FIG. 2B shows the effect of polyanionic oligosaccharide on transfection of HeLa cells—no uptake of nucleic acids is observed in the absence of oligosaccharide (medium thickness line), however significant uptake is observed when oligosaccharide is present (thickest line).

These data indicate that treatment with polyanionic oligosaccharide increases the efficiency of transfection of nucleic acids into cells.

The invention claimed is:

1. A pharmaceutical composition comprising a non-immunogenic net polyanionic 3- to 28-mer oligouronate associated with a particulate complex of an anionic nucleic acid material and a cationic macromolecule, together with at least one pharmaceutical carrier or excipient, wherein said composition is suitable for parenteral administration of a gene present in said nucleic acid material to a human or non-human vertebrate animal subject.

2. A composition as claimed in claim 1, further comprising wherein said particulate complex is a lipoplex.

3. A composition as claimed in claim 1, further comprising wherein said particulate complex is a polyplex.

4. A composition as claimed in claim 1 wherein the oligouronate is linear.

5. A composition as claimed in claim 1 wherein the oligouronate is a 4- to 25-mer.

6. A composition as claimed in claim 1 wherein the oligouronate has a molecular weight in the range 350 to 6000 Da.

7. A composition as claimed in claim 1 wherein the oligouronate has a viscosity of less than 20 cP when measured under standard conditions (C=1%, $H_2O$).

8. A composition as claimed in claim 1 wherein the oligounonate has been produced from alginate.

9. A composition as claimed in claim 1 wherein the oligouronate is oligoguluronic acid.

10. A method for delivery of a gene to a human or non-human vertebrate animal subject in need thereof comprising parenterally administering to said subject an effective amount of a composition according to claim 1.

11. The method of claim 10 wherein said gene therapy is for the treatment of a cancer, thasassemia, cystic fibrosis, deafness, a vision disorder, diabetes, Huntington's disease, X-linked severe combined immunodeficiency disease, heart disease or ornithine transcarboxylase deficiency.

12. The method of claim 11, wherein said cancer is a myeloid disorder.

13. The method of claim 11, wherein said vision disorder is Leber's congenital amaurosis.

* * * * *

UNITED STATES PATENT AND TRADEMARK OFFICE
CERTIFICATE OF CORRECTION

PATENT NO. : 8,987,215 B2  
APPLICATION NO. : 13/259124  
DATED : March 24, 2015  
INVENTOR(S) : Catherine Taylor Page 1 of 1

It is certified that error appears in the above-identified patent and that said Letters Patent is hereby corrected as shown below:

On the title page
    In column 1 (page 2, Item 56) at line 35, References Cited Under Other Publications, change "Pharaceutical" to --Pharmaceutical--.
    In column 2 (page 2, Item 56) at line 22, References Cited Under Other Publications, change "Water-soluable" to --Water soluble--.

In the specification
    In column 4 at line 1, change "has a," to --has a--.
    In column 4 at line 28, change "manuronic" to --mannuronic--.
    In column 5 at line 46 (approx.), change "Infection" to --Injection--.
    In column 5 at line 61 (approx.), change "Infection" to --Injection--.
    In column 7 at line 13, change "fluorphore." to --fluorophore.--.

In the claims
    In column 8 at lines 16-17, in claim 8, change "oligounonate" to --oligouronate--.
    In column 8 at line 25, in claim 11, change "thasassemia," to --thalassemia,--.

Signed and Sealed this
Eighth Day of December, 2015

Michelle K. Lee
*Director of the United States Patent and Trademark Office*